United States Patent [19]

Liu

[11] Patent Number: 4,849,548
[45] Date of Patent: Jul. 18, 1989

[54] HYDROLYSIS OF HALO- AND ALKYL-SUBSTITUTED PHENOLS

[75] Inventor: Ming-Biann Liu, Midland, Mich.

[73] Assignee: The Dow Chemical Company, Midland, Mich.

[21] Appl. No.: 170,486

[22] Filed: Mar. 21, 1988

[51] Int. Cl.⁴ .................. C07C 39/11; C07C 39/27
[52] U.S. Cl. ................................ 568/764; 568/765; 568/766; 568/770; 568/774
[58] Field of Search ............. 568/774, 764, 770, 765

[56] References Cited

U.S. PATENT DOCUMENTS 4,731,423  3/1988  Mondoza et al. .................. 525/480

OTHER PUBLICATIONS

Mendoza et al., *Meta–Halo–Phenolic Alkylation Products and Epoxy Systems*, U.S. Pat. No. 4,731,423 (Mar. 15, 1988).

Auwers et al., "Ueber Anhydro-p-Oxymesitylalkohol und Seine Umwaldungsproduct", 302 Ann. Chemie 76 (1898) (Translation Attached).

Auwers et al., "Ueber Dibrom-p-Oxymesitylalkohol", 32 Berichte 3309 (1899) (Translation Attached).

*Primary Examiner*—Werren B. Lone

[57] ABSTRACT

A 4-halomethyl-3,5-dihalo-2,6-dialkylphenol is hydrolyzed by contact with water to form a 4-hydroxy-methyl-3,5-dihalo-2,6-dialkylphenol under conditions to minimize formation of the corresponding bis-(4-hydroxy-3,5-dialkyl-2,6-dihalobenzyl) ether.

11 Claims, No Drawings

HYDROLYSIS OF HALO- AND ALKYL-SUBSTITUTED PHENOLS

BACKGROUND OF THE INVENTION

The present invention relates to the art of producing substituted phenols. It relates more specifically to the art of hydrolyzing halogenated substituted phenols, particularly brominated mesitols.

Halogenated dihydroxy aromatic compounds are useful intermediates and curing agents for flame retardant epoxy resins. See, e.g., Mendoza, *Brominated Hydroxyaromatic Compounds*, U.S. Pat. No. 4,621,159 Nov. 4, 1986); Silvis et al., *Brominated Epoxyaromatic Compounds*, U.S. Pat. No. 4,661,644 (Apr. 28, 1987); Mendoza, *Brominated Hydroxyaromatic Compounds*, U.S. Pat. No. 4,705,901 (Nov. 10, 1987); Berman, *Halogenated Epoxy Resins*, U.S. Pat. No. 4,727,119 (Feb. 23, 1988); and Mendoza et al., *Meta-Halo-Phenolic Alkylation Products and Epoxy Systems*, U.S. Pat. No. 4,731,423 (Mar. 15, 1988), which are incorporated herein by reference.

In particular, 4-hydroxymethyl-dihalo-dialkylphenols (hereinafter referred to as 4-hydroxymethylphenols) are preferred reagents for making cured epoxy resins. Mendoza et al., *Meta-Halo-Phenolic Alkylation Products and Epoxy Systems*, U.S. Pat. No. 4,731,423 (Mar. 15, 1988). 4-hydroxymethylphenols are prepared in a twostep process from 4-methyl-dialkylphenols, such as mesitol. First, the 4-methyl-dialkylphenol is halogenated with a halogenating agent such as molecular bromine to form a 4-halomethyl-dihalo-dialkylphenol (hereinafter referred to as 4-halomethylphenol), according to a process such as that described in Mendoza, *Di-ortho-substituted Di-meta-halogenated Para-halomethylphenols*, U.S. Pat. No. 4,684,752 (Aug. 4, 1987). Second, the 4-halomethylphenol undergoes hydrolysis to form the 4-hydroxymethylphenol according to the process described in Auwers, et al., "Anhydro-p-hydroxymesityl Alcohol and its Conversion Products", 302 Ann. Chem. 76 (1898) and Auwers, et al., "Ueber Dibrom-p-oxymesitylalkohol," 32 *Chem. Berichte* 3309 (1899).

In actual practice, the synthesis described above gives a mixture of products. First, halogenation of 4-methyl-2,6-dialkylphenols yields some 2-halogenated product. For instance, halogenation of mesitol with bromine, produces ortho- and para-tribromomesitol and tetrabromomesitol illustrated below.

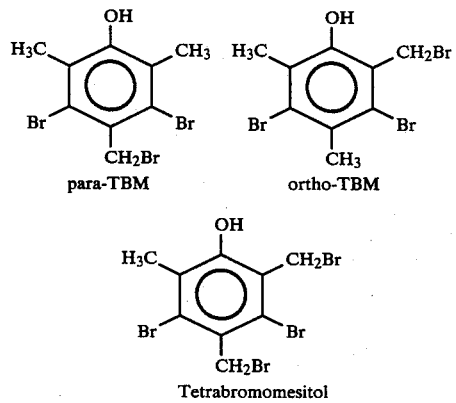

para-TBM  ortho-TBM

Tetrabromomesitol

Second, hydrolysis of the halomethylphenol mixture permits further side reactions. In one side reaction hydroxymethylphenol product reacts with halomethylphenol reagent to form a bis-(4-hydroxy-2,6 dihalo-3,5-dialkylbenzylic) ether (hereinafter referred to as ether). In another side reaction, the halomethylphenol or hydroxymethylphenol can react with the solvent to form side products.

For instance, hydrolysis of the previously described halogenated mesitol mixture in acetone yields ortho- and para-dibromomesitol benzyl alcohol (DBMBA), di-hydroxymethyl-dibromomesitol (DHDBM), di-bromomesitylbenzyl ether (DBMBE) and side products, such as acetyl derivatives caused by reaction of ortho-DBMBA and DHDBM with acetone. The product mixture from the hydrolysis is illustrated below.

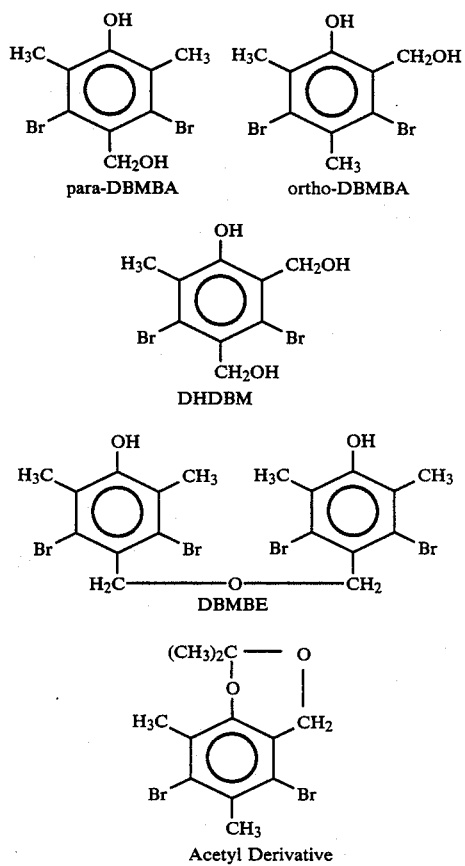

para-DBMBA  ortho-DBMBA

DHDBM

DBMBE

Acetyl Derivative

All of the products which contain at least two hydroxyl groups can be used to make cured epoxy resins. Even acetyl derivatives and other side products, which do not form resins, do not seriously degrade the resins if in low concentrations. However, the most desirable properties are obtained from 4-hydroxymethylphenol in which the concentrations of ether and acetyl derivatives are minimized. Suitable reagent mixtures can be achieved following the processes of Auers et al. and purifying the final product. Such purifications require extra steps and expenses in the epoxy resin synthesis. It would be preferable to form the hydroxymethylphenol in a process which holds the production of ether and side products down to a level which is acceptable for use without purification.

SUMMARY OF THE INVENTION

The present invention is a process for synthesizing a hydroxymethyl-dihalo-dialkylphenol (hydroxymethylphenol) comprising the step of contacting a halomethyl-dihalo-dialkylphenol (halomethylphenol) with a substantial excess of water in a water-miscible organic solvent at a temperature of less than 55° C. under conditions such that a hydroxymethylphenol is formed. The process of the present invention hydrolyzes the halomethylphenol but holds the production of ether and acetyl derivatives or other side products down to a level acceptable for further use without purification. The hydroxymethylphenols thus produced can be used to form useful epoxy resins as previously described and can also be incorporated into polyesters.

DETAILED DESCRIPTION OF THE INVENTION

Halomethylphenols hydrolyzed in the process of the present invention are phenols substituted with two halogen atoms, two alkyl groups, and one halomethyl group. The halogens present in the substituted phenolic compounds are preferably chlorine or bromine and more preferably bromine. They alkyl groups are preferably hexyl or smaller, more preferably ethyl or methyl and most preferably methyl. Preferably, the halogen atoms are meta to the phenolic hydroxyl group and the alkyl and halomethyl groups are *ortho* and *para* to the phenolic hydroxyl group. In its most preferred embodiments, the halomethylphenol is *para*-tribromomesitol (*para*-TBM).

The preferred process for making halomethylphenol is that described in Mendoza, *Di-ortho-substituted Di-meta-halogenated Para-halomethylphenols*, U.S. Pat. No. 4,684,752 (Aug. 4, 1987), which is incorporated herein by reference. In the process of Mendoza, preferred halomethylphenols are made by halogenation of a 4-methyl-2,6-dialkylphenol or a 4-methyl-3,5-dihalo-2,6-dialkylphenol (both groups herein after called methylphenols). The methylphenol is most preferably mesitol or dibromomesitol. The methylphenol is preferably contacted with a halogenating agent such as molecular bromine in an aprotic solvent such as bromochloromethane at a temperature between about 25° C. and about 85° C. for a period of about 2 to 5 hours. Selectivity to para-halomethylphenol, which is important to maximize yields of para-hydroxymethylphenol, is preferably at least about 90 percent, more preferably at least about 95 percent. Other known processes are described in Auwers and Allendorf, 302 *Ann. Chemie* 76 (1898); Auwers and Rapp, 302 *Chemie*, 153 (1898); Fries and Brandes, 542 *Ann. Chemie* 48 (1939); and Auwers and Traum, 302 Ann. Chemie 3309 (1899), which are incorporated herein by reference.

Hydrolysis of the halomethylphenol involves several competing reactions. First, the halomethylphenol reacts with water to yield the corresponding hydroxymethylphenol and a molecule of hydrogen halide. Second, the hydroxymethylphenol reacts further with unreacted halomethyphenol to form hydroxybenzylic ether. Third, halo- and hydroxymethylphenols react with solvents and impurities to form further impurities, such as acetyl derivatives. The rate constant for the ether formation reaction is substantially faster than the rate constant for the hydrolysis reaction, and the difference between reaction rates widens with increasing temperature. It is therefore necessary to accelerate conversion of halomethylphenol and to keep temperatures as low as feasible to limit ether formation.

Hydrolysis takes place in a substantial excess of water to accelerate the conversion of halomethylphenol. Water used in the present process is preferably no more than about 0.2N acidic or basic. The water is more preferably about neutral. More acidic or basic solutions generate substantial amounts of unidentified impurities and lower the yield of the desired hydroxymethylphenol. The molar ratio of water to halomethylphenol is preferably at least about 30:1 and more preferably about 40:1. When the halomethylphenol being hydrolyzed is tribromomesitol, the ratio by weight of water to tribromomesitol is preferably at most about 4:1 and at least about 2:1. Greater excesses of water provide a some improvement in selectivity but may reduce the efficiency of the process since the ratio of water permits only small amounts of halomethylphenol in the reactor at any one time.

Hydrolysis takes place in a solvent which will dissolve the halomethylphenol compound and which is miscible with water. Preferred solvents comprise acetone, THF, dioxan, n-methylpyrrolidone, dimethylsulfoxide or dimethoxyethane. The most preferred solvent is acetone. Water and the solvent must be maintained in a single phase state since unidentified by-products are formed if aqueous and organic layers separate during the reaction. The amount of solvent should also be sufficient to dissolve not only the halomethylphenol but also substantial amounts of water. The amount of solvent is preferably at least about 0.35 mole of solvent per mole of water. It is also preferably at least about 10 moles of solvent per mole of halomethylphenol. When hydrolyzing tribromomesitol in acetone, the preferred weight ratio of acetone to water to tribromomesitol is about $2.5+:2.0:1.0$.

The temperature of the hydrolysis is preferably kept as low as possible without the product binding up the stirrer. The temperature is preferably no more than about 50° C. and most preferably no more than about 45° C. The temperature is preferably no less than about 20° C. and more preferably no less than about 40° C. Most preferably, water is added at a temperature of about 20° C., and the temperature is raised gradually to between 40° C. and 45° C. The pressure of the reaction is preferably about ambient pressure. Due to the lower reaction temperature, the time for the hydrolysis to run to completion may be longer in the process of the present invention.

Highest yields and selectivity are obtained by isolating the halomethylphenol after halogenation and before hydrolysis. For the purposes of industrial efficiency, however, it is often preferable to perform a one-pot synthesis from methylphenol to hydroxymethylphenol without isolating the intermediate halomethylphenol. In such cases, it is important to remove substantially all of the halogenation solvent before proceeding to hydrolysis. Solvents such as haloalkanes used in the halogenation step decrease the selectivity of the hydrolysis step toward the hydroxymethylphenol and increase the levels of ether formation.

The affinity of the halomethylphenol for haloalkane solvents is high enough that those solvents cannot be removed simply by distillation or vacuum stripping. However, excess solvent is removed by vacuum stripping until a thick slurry forms. Thereafter, an excess of acetone is added and the remaining halogenation solvent is removed by codistillation with the acetone. The excess of acetone is preferably at least about 1.5 moles for each mole of halomethylphenol. When the halomethylphenol is tribromomesitol, the weight ratio of acetone to halomethylphenol is preferably at least 0.25:1. It has surprisingly been discovered that, despite the low boiling point of acetone, the halogenation solvent can be removed in this manner, while the halomethylphenol remains in a thick slurry with acetone. Thereafter, more hydrolysis solvent is added to complete the hydrolysis step.

When the reagent mixture comprises primarily halomethylphenol, the major product of the instant process is a hydroxymethyl-dihalo-dialkylphenol. Preferably, the product is a hydroxymethyl-dialkyl-3,5-dihalophenol. More preferably, the product is a 4-hydroxymethyl-3,5-dihalo-2,6-dimethylphenol. Most preferably, the product is 4-hydroxymethyl-3,5-dibromo-2,6-dimethylphenol (dibromomesitol benzyl alcohol).

The proportion of 4-hydroxymethylphenol with respect to 2-hydroxymethylphenol and 2,4-dihydroxymethylphenol in the product mixture is dependent upon the proportion of 4-halomethylphenol with respect to other halogenated phenols in the reagent mixture. Generally, acetyl derivatives are not formed in measurable amounts from purified 4-halomethylphenol from which other isomers have been removed, but when using unpurified halomethylphenol, hydrolysis conditions of the present invention can significantly reduce acetyl derivative formation. Likewise, ether formation is effected by the presence of other isomers or compounds, but reaction conditions of the present invention can significantly limit ether formation.

Using a process of the present invention, a composition can be formed which comprises no more than about 20 percent ether, no more than about 7 percent acetyl derivatives and other impurities and no less than about 70 percent 4-hydroxymethylphenol. Preferably, the ether is no more than 13 molar percent of the total product. More preferably, it is no more than about 10 percent and most preferably no more than about 8 percent. In a process hydrolyzing unpurified halomethylphenol, the selectivity to hydroxymethylphenol is preferably at least about 84 percent by mole; more preferably, at least about 90 percent. The production of acetyl derivatives is preferably no more than about 8 percent by mole; more preferably, no more than about 6 percent; and most preferably, no more than about 3 percent.

ILLUSTRATIVE EXAMPLES

The following examples are for illustrative purposes only and are not to be taken as limiting either the specification or the claims. All ratios and proportions are by mole unless otherwise indicated.

EXAMPLE 1

One-pot Synthesis of DBMBA

A 5-liter, 3-necked, round-bottom flask is equipped with a Vigreaux distillation column, a mechanical stirrer, a dropping funnel, a thermometer and a heating mantle. Mesitol (99 percent, 252 g) is dissolved in 1233 g of bromochloromethane. Bromine (976 g) is added through the dropping funnel over a period of about 60 minutes. The temperature is increased from about 20° C. to about 68° C. at which reflux occurs. After about 5½ hours at reflux, excess bromine is vacuum stripped and any residual bromine is neutralized using propylene. The slurry is cooled to about 20° C. and the remaining bromochloromethane is removed by vacuum stripping, followed by codistillation with 750 g of acetone.

At room temperature, 1600 g of acetone is added to the dissolved tribromomesitol and then 1375 g of water is added. The temperature is gradually increased from 25° C. to 50° C. and remains at 50° C. for about 3 hours. The acetone is removed by vacuum stripping and the slurry is filtered. The solid is washed with water until the water wash becomes neutral and is subsequently washed with 300 ml of 1N sodium hydroxide. The product is dried at 70° C. for 24 hours.

The process yields 562 g of product. The product contains 1.5 percent 3,5-dibromo-4,6-dimethyl-2-hydroxymethylphenol, 1.6 percent acetyl derivatives of tribromomesitol, 4.3 percent 2,4-bis-hydroxymethyl-3,5-dibromo-6-methylphenol, 12.2 percent 2,6-dibromo-3,5-dimethyl-4-hydroxybenzyl ether and 80.4 percent 3,5-dibromo-2,6-dimethyl-4-hydroxymethylphenol.

EXAMPLE 2

Comparative Synthesis of DBMBA Using Unpurified TBM

Mesitol (150 g) is dissolved in 370 ml of bromochloromethane in a 3-liter, three-necked round-bottom flask equipped with a reflux condenser, a mechanical agitator, a dropping funnel and a heating mantle. The solution is heated to reflux over about 1 hour (about 68° C. to 74° C.) while 581 g of bromine is added through the dropping funnel. Reflux is maintained for about 5 hours and then the solution is cooled to about 60° C. Hexene (20 g) is added to neutralize excess bromine and the solvent is removed under reduce pressure in a rotary evaporator. When the product is in solid form, 100 ml of acetone is added and removal of the solvent is continued. Addition of acetone and removal of the solvent is repeated three more times. Then the solid is transferred to a dish and dried in a vacuum oven at 40° C. for 18 hours. A light yellow solid (429 g) is recovered.

The product (20 g) is dissolved in 120 ml of acetone. Water (80 ml) is added at room temperature and then the temperature of the reaction is increased through a range of 24° C. to 34° C. The high temperature is maintained until GLC analysis shows that the reaction is essentially complete after about 320 minutes. The products are analyzed by GLC, which shows the proportions of products set out in Table I. The process is repeated three more times using the reagents and reaction conditions set out in Table I.

TABLE I

| Sample | TBM (g) | Acetone (ml) | Water (ml) | Temp (°C.) | Time (min) | DBMBA (%) | DBMBE (%) | Other (%) |
|---|---|---|---|---|---|---|---|---|
| 1 | 20 | 120 | 80 | 24–34 | 320 | 92.27 | 5.01 | 2.72 |
| 2 | 40 | 120 | 80 | 21–38 | 320 | 83.93 | 8.47 | 7.61 |
| 3 | 20 | 120 | 80 | 58–64* | 90 | 87.19 | 4.80 | 8.01 |
| 4 | 40 | 120 | 80 | 58–64* | 90 | 79.46 | 11.04 | 9.50 |

*Not an example of the invention

The results show that the process of the present invention minimizes the total proportions of ether and side products and maximizes the proportions of DBMBA in the product mixture.

EXAMPLE 3

Comparative Hydrolysis of Purified TBM

At least 99 percent pure para-TBM (20 g) is dissolved in 120 ml of acetone. Water (80 ml) is added at room temperature and then the temperature of the reaction is increased through a range of 24° C. to 47° C. The high temperature is maintained until GLC analysis shows that the reaction is essentially complete after about 120 minutes. The products are analyzed by GLC, which shows the proportions of products set out in Table II. The process is repeated five more times using the reagents and reaction conditions set out in Table II.

TABLE II

| Sample | TBM (g) | Acetone (ml) | Water (ml) | Temp (°C.) | Time (min) | DBMBA (%) | DBMBE (%) |
|---|---|---|---|---|---|---|---|
| 5 | 20 | 120 | 80 | 24–47 | 120 | 93.55 | 6.45 |
| 6 | 20 | 120 | 80 | 27 | 320 | 94.39 | 5.61 |
| 7 | 20 | 120 | 80 | 58–64* | 90 | 91.66 | 8.34 |
| 8 | 40 | 120 | 80 | 24–47 | 120 | 90.58 | 9.42 |
| 9 | 40 | 120 | 80 | 27 | 320 | 94.56 | 5.44 |
| 10 | 40 | 120 | 80 | 58–64* | 90 | 86.33 | 13.67 |

*Not an example of the invention

The results show that the selectivity of DBMBA and away from DBMBE is greater for the process of the present invention than for the process under prior art conditions.

What is claimed is:

1. A process for synthesizing a hydroxymethyl-dihalo-dialkylphenol comprising the step of contacting a halomethyl-dihalo-dialkylphenol, wherein each said alkyl group comprises not more than about six carbon atoms, with a substantial excess of water in a water-miscible organic solvent at a temperature of less than 55° C. under conditions such that a hydroxymethyl-dihalo-dialkylphenol is formed.

2. A process of claim 1 wherein the reaction mixture comprises at least about 30 moles of water per mole of halomethyl-dihalo-dialkylphenol and the amount of solvent is sufficient to prevent formation of separate aqueous and organic phases.

3. A process of claim 2 wherein the reaction mixture comprises at least about 0.35 mole of solvent per mole of water.

4. A process of claim 3 wherein each halogen on the halomethyl-dihalo-dialkylphenol and the hydroxymethyl-dihalo-dialkylphenol is independently chlorine or bromine and wherein the temperature of the reaction is not more than about 50° C.

5. A process of claim 4 wherein the halomethyl-dihalo-dialkylphenol is tribromomesitol and dibromomesitol benzyl alcohol.

6. A process of claim 5 wherein the solvent comprises acetone, THF, n-methylpyrrolinone, dimethylsulfoxide, dioxan or dimethoxyethane.

7. A process of claim 6 wherein the solvent is acetone.

8. A process of claim 7 wherein the temperature of the process is at least about 20° C.

9. A process of claim 8 wherein the final product comprises by mole no more than about 10 percent dibromomesityl benzyl ether, and no more than about 8 percent acetyl derivatives of tribromomesitol.

10. A process of claim 9 wherein the final product comprises by mole no more than about 8 percent dibromomesityl benzyl ether, and no more than about 6 percent acetyl derivatives of tribromomesitol.

11. A process of claim 10 wherein the final product comprises no more than about 3 percent acetyl derivatives of tribromomesitol.

* * * * *